(12) United States Patent
Zucherman et al.

(10) Patent No.: US 7,476,251 B2
(45) Date of Patent: *Jan. 13, 2009

(54) INTERSPINOUS PROCESS APPARATUS AND METHOD WITH A SELECTABLY EXPANDABLE SPACER

(75) Inventors: James F. Zucherman, San Francisco, CA (US); Ken Y. Hsu, San Francisco, CA (US); Charles J. Winslow, Walnut Creek, CA (US)

(73) Assignee: Kyphon SARL, Neuchatel (CH)

( * ) Notice: Subject to any disclaimer, the term of this patent is extended or adjusted under 35 U.S.C. 154(b) by 81 days.

This patent is subject to a terminal disclaimer.

(21) Appl. No.: 11/556,653

(22) Filed: Nov. 3, 2006

(65) Prior Publication Data

US 2007/0106385 A1    May 10, 2007

Related U.S. Application Data

(63) Continuation of application No. 10/684,847, filed on Oct. 14, 2003, now Pat. No. 7,306,628.

(60) Provisional application No. 60/421,921, filed on Oct. 29, 2002.

(51) Int. Cl.
  *A61F 2/44* (2006.01)
  *A61B 17/70* (2006.01)
(52) U.S. Cl. .................. 623/17.15; 623/17.13; 606/248
(58) Field of Classification Search ... 623/17.11–17.16; 606/61, 248, 249
See application file for complete search history.

(56) References Cited

U.S. PATENT DOCUMENTS

| | | | |
|---|---|---|---|
| 2,456,806 A | 12/1948 | Wolffe | 33/174 |
| 2,677,369 A | 5/1954 | Knowles | 128/92 |
| 3,426,364 A | 2/1969 | Lumb | 3/1 |
| 3,643,658 A | 2/1972 | Steinemenan | 128/920 |
| 3,648,691 A | 3/1972 | Lumb | 128/920 |
| 3,867,728 A | 2/1975 | Stubstad | 3/1 |
| 3,875,595 A | 4/1975 | Froning | 3/1 |
| 4,034,418 A | 7/1977 | Jackson | 3/1.911 |
| 4,219,015 A | 8/1980 | Steinemenan | 128/92 D |
| 4,309,777 A | 1/1982 | Patil | 3/1.91 |
| 4,349,921 A | 9/1982 | Kuntz | 3/1 |
| 4,369,769 A | 1/1983 | Edwards | 128/69 |
| 4,401,112 A | 8/1983 | Rezaian | 128/92 B |

(Continued)

FOREIGN PATENT DOCUMENTS

CA    2015507    1/1991

(Continued)

OTHER PUBLICATIONS

Minns, R.J., et al., "Preliminary Design and Experimental Studies of a Novel Soft Implant for Correcting Sagittal Plane Instability in the Lumbar Spine," Spine, vol. 22, No. 16, pp. 1819-1825, Lippincott-Raven Publishers (1997).

(Continued)

*Primary Examiner*—Pedro Philogene
(74) *Attorney, Agent, or Firm*—Coats and Bennett PLLC

(57) ABSTRACT

The present invention is an interspinous process implant with a selectably expandable spacer that can be placed between adjacent spinous processes.

23 Claims, 9 Drawing Sheets

U.S. PATENT DOCUMENTS

| | | | | |
|---|---|---|---|---|
| 4,455,690 | A | 6/1984 | Homsy | 3/1 |
| 4,479,491 | A | 10/1984 | Martin | 128/92 B |
| 4,501,269 | A | 2/1985 | Bagby | 128/96 G |
| 4,502,161 | A | 3/1985 | Wall | 623/18 |
| 4,553,273 | A | 11/1985 | Wu | 623/18 |
| 4,554,914 | A | 11/1985 | Kapp | 128/92 C |
| 4,599,084 | A | 7/1986 | Nashef | 623/16 |
| 4,599,086 | A | 7/1986 | Doty | 623/17 |
| 4,604,995 | A | 8/1986 | Stephens | 128/69 |
| 4,611,582 | A | 9/1986 | Duff | 128/69 |
| 4,636,217 | A | 1/1987 | Ogilvie | 623/17 |
| 4,643,178 | A | 2/1987 | Nastari | 128/92 |
| 4,657,550 | A | 4/1987 | Daher | 623/17 |
| 4,685,447 | A | 8/1987 | Iversen | 128/1 R |
| 4,696,290 | A | 9/1987 | Steffee | 128/69 |
| 4,714,469 | A | 12/1987 | Kenna | 623/17 |
| 4,743,256 | A | 5/1988 | Brantigan | 623/17 |
| 4,772,287 | A | 9/1988 | Ray | 623/17 |
| 4,790,303 | A | 12/1988 | Steffee | 128/924 M |
| 4,834,757 | A | 5/1989 | Brantigan | 623/17 |
| 4,878,915 | A | 11/1989 | Brantigan | 623/17 |
| 4,904,260 | A | 2/1990 | Ray | 623/17 |
| 4,904,261 | A | 2/1990 | Dove | 623/17 |
| 4,913,134 | A | 4/1990 | Luque | 128/69 |
| 4,923,471 | A | 5/1990 | Morgan | 623/16 |
| 4,932,975 | A | 6/1990 | Main | 623/17 |
| 4,936,848 | A | 6/1990 | Bagby | 623/17 |
| 4,946,378 | A | 8/1990 | Hirayama | 623/17 |
| 4,961,740 | A | 10/1990 | Ray | 606/61 |
| 4,969,888 | A | 11/1990 | Scholten | 606/94 |
| 5,011,484 | A | 4/1991 | Breard | 606/61 |
| 5,015,247 | A | 5/1991 | Michelson | 606/61 |
| 5,015,255 | A | 5/1991 | Kuslich | 623/17 |
| 5,026,373 | A | 6/1991 | Ray | 606/61 |
| 5,035,716 | A | 7/1991 | Downey | 623/17 |
| 5,047,055 | A | 9/1991 | Bao | 623/17 |
| 5,055,104 | A | 10/1991 | Ray | 606/61 |
| 5,059,193 | A | 10/1991 | Kuslich | 606/61 |
| 5,059,194 | A | 10/1991 | Michelson | 606/61 |
| 5,062,845 | A | 11/1991 | Kuslich | 606/80 |
| 5,062,850 | A | 11/1991 | MacMillan | 623/17 |
| 5,074,864 | A | 12/1991 | Cozad | 606/54 |
| 5,084,049 | A | 1/1992 | Asher et al. | 606/61 |
| 5,088,869 | A | 2/1992 | Greenslade | 411/386 |
| 5,092,866 | A | 3/1992 | Breard | 606/61 |
| 5,105,255 | A | 4/1992 | Shannon | 357/68 |
| 5,122,130 | A | 6/1992 | Keller | 606/61 |
| 5,123,926 | A | 6/1992 | Pisharodi | 623/17 |
| 5,127,912 | A | 7/1992 | Ray | 606/61 |
| 5,147,404 | A | 9/1992 | Downey | 623/17 |
| 5,167,662 | A | 12/1992 | Hayes | 606/61 |
| 5,167,665 | A | 12/1992 | McKinney | 606/75 |
| 5,180,381 | A | 1/1993 | Aust | 606/61 |
| 5,192,327 | A | 3/1993 | Brantigan | 623/17 |
| 5,258,031 | A | 11/1993 | Salib | 623/17 |
| 5,263,953 | A | 11/1993 | Bagby | 606/61 |
| 5,275,601 | A | 1/1994 | Gogolewski | 606/72 |
| 5,290,312 | A | 3/1994 | Kojimoto | 623/17 |
| 5,300,073 | A | 4/1994 | Ray | 606/61 |
| 5,304,178 | A | 4/1994 | Stahurski | 606/61 |
| 5,306,275 | A | 4/1994 | Bryan | 606/61 |
| 5,306,309 | A | 4/1994 | Wagner | 623/17 |
| 5,352,225 | A | 10/1994 | Yuan | 606/61 |
| 5,366,455 | A | 11/1994 | Dove | 606/61 |
| 5,387,213 | A | 2/1995 | Breard | 606/61 |
| 5,390,683 | A | 2/1995 | Pisharodi | 128/898 |
| 5,391,168 | A | 2/1995 | Sanders | 606/61 |
| 5,395,372 | A | 3/1995 | Holt | 606/61 |
| 5,415,661 | A | 5/1995 | Holmes | 606/69 |
| 5,437,672 | A | 8/1995 | Alleyne | 606/61 |
| 5,443,514 | A | 8/1995 | Steffee | 623/17 |
| 5,454,812 | A | 10/1995 | Lin | 606/61 |
| 5,456,722 | A | 10/1995 | McLeod | 623/13 |
| 5,458,638 | A | 10/1995 | Kuslich | 623/17 |
| 5,458,641 | A | 10/1995 | Jimenez | 623/17 |
| 5,458,643 | A | 10/1995 | Oka | 623/18 |
| 5,468,242 | A | 11/1995 | Reisberg | 606/69 |
| 5,470,333 | A | 11/1995 | Ray | 606/61 |
| 5,491,882 | A | 2/1996 | Walston | 29/419.1 |
| 5,496,318 | A | 3/1996 | Howland | 606/61 |
| 5,505,732 | A | 4/1996 | Michelson | 606/61 |
| 5,507,745 | A | 4/1996 | Logroscino | 606/61 |
| 5,507,823 | A | 4/1996 | Walston | 623/21 |
| 5,514,180 | A | 5/1996 | Heggeness | 623/17 |
| 5,527,312 | A | 6/1996 | Ray | 606/61 |
| 5,531,747 | A | 7/1996 | Ray | 606/61 |
| 5,534,028 | A | 7/1996 | Bao | 623/17 |
| 5,534,029 | A | 7/1996 | Shima | 623/17 |
| 5,540,689 | A | 7/1996 | Sanders | 606/61 |
| 5,549,679 | A | 8/1996 | Kuslich | 623/17 |
| 5,554,191 | A * | 9/1996 | Lahille et al. | 623/17.11 |
| 5,562,736 | A | 10/1996 | Ray | 623/17 |
| 5,571,191 | A | 11/1996 | Fitz | 623/17 |
| 5,577,995 | A | 11/1996 | Walker | 601/120 |
| 5,584,832 | A | 12/1996 | Schlapfer | 606/61 |
| 5,593,409 | A | 1/1997 | Michelson | 606/61 |
| 5,601,553 | A | 2/1997 | Trebing | 606/61 |
| 5,603,713 | A | 2/1997 | Aust | 606/61 |
| 5,609,634 | A | 3/1997 | Voydeville | 623/17 |
| 5,616,142 | A | 4/1997 | Yuan | 606/61 |
| 5,623,984 | A | 4/1997 | Nozaki | 164/457 |
| 5,628,756 | A | 5/1997 | Barker, Jr. | 606/139 |
| 5,645,597 | A | 7/1997 | Krapiva | 623/17 |
| 5,645,599 | A | 7/1997 | Samani | 623/17 |
| 5,653,761 | A | 8/1997 | Pisharodi | 623/17 |
| 5,658,286 | A | 8/1997 | Sava | 606/61 |
| 5,672,177 | A | 9/1997 | Seldin | 606/71 |
| 5,674,295 | A | 10/1997 | Ray | 623/17 |
| 5,674,296 | A | 10/1997 | Bryan | 623/17 |
| 5,676,702 | A | 10/1997 | Ratron | 623/17 |
| 5,702,455 | A | 12/1997 | Saggar | 623/17 |
| 5,725,582 | A | 3/1998 | Bevan | 623/17 |
| 5,741,261 | A | 4/1998 | Moskovitz | 606/79 |
| 5,766,251 | A | 6/1998 | Koshino | 623/16 |
| 5,766,252 | A | 6/1998 | Henry | 623/17 |
| 5,800,438 | A | 9/1998 | Tuke | 606/90 |
| 5,824,098 | A | 10/1998 | Stein | 623/20 |
| 5,836,948 | A | 11/1998 | Zucherman | 606/61 |
| 5,860,977 | A | 1/1999 | Zucherman | 606/61 |
| 5,865,846 | A | 2/1999 | Bryan | 623/17 |
| 5,876,402 | A | 3/1999 | Errico | 606/61 |
| 5,876,404 | A | 3/1999 | Zucherman | 606/61 |
| 5,879,396 | A | 3/1999 | Walston | 623/21 |
| 5,885,299 | A | 3/1999 | Winslow | 606/99 |
| 5,888,224 | A | 3/1999 | Beckers | 627/17 |
| 5,888,226 | A | 3/1999 | Rogozinski | 623/17 |
| 5,951,555 | A | 9/1999 | Rehak | 606/61 |
| 5,976,186 | A | 11/1999 | Bao | 623/17 |
| 6,001,130 | A | 12/1999 | Bryan | 623/17 |
| 6,022,376 | A | 2/2000 | Assell | 623/17 |
| 6,030,162 | A | 2/2000 | Huebner | 411/413 |
| 6,045,552 | A | 4/2000 | Zucherman | 606/61 |
| 6,045,554 | A | 4/2000 | Grooms | 606/73 |
| 6,048,204 | A | 4/2000 | Klardie | 433/174 |
| 6,048,342 | A | 4/2000 | Zucherman | 606/61 |
| 6,048,344 | A | 4/2000 | Schenk | 606/73 |
| 6,068,630 | A | 5/2000 | Zucherman | 606/61 |
| RE36,758 | E | 6/2000 | Fitz | 623/17 |
| 6,074,390 | A | 6/2000 | Zucherman | 606/61 |
| 6,090,112 | A | 7/2000 | Zucherman | 606/61 |
| 6,099,531 | A | 8/2000 | Bonutti | 606/87 |
| 6,113,639 | A | 9/2000 | Ray | 623/17.16 |
| 6,129,730 | A | 10/2000 | Bono | 606/73 |
| 6,132,464 | A | 10/2000 | Martin | 623/17 |

| | | | |
|---|---|---|---|
| 6,139,550 A | 10/2000 | Michelson | 606/69 |
| 6,149,652 A | 11/2000 | Zucherman | 606/61 |
| 6,152,926 A | 11/2000 | Zucherman | 606/61 |
| 6,152,927 A | 11/2000 | Farris | 606/69 |
| 6,156,038 A | 12/2000 | Zucherman | 606/61 |
| 6,156,067 A | 12/2000 | Bryan | 623/17.15 |
| 6,183,471 B1 | 2/2001 | Zucherman | 606/61 |
| 6,190,387 B1 | 2/2001 | Zucherman | 606/61 |
| 6,190,414 B1 * | 2/2001 | Young et al. | 623/17.15 |
| 6,193,721 B1 | 2/2001 | Michelson | 606/70 |
| 6,200,322 B1 | 3/2001 | Branch | 606/96 |
| 6,206,922 B1 | 3/2001 | Zdeblick | 623/17.11 |
| 6,217,580 B1 | 4/2001 | Levin | 606/71 |
| 6,224,602 B1 | 5/2001 | Hayes | 606/69 |
| 6,224,607 B1 | 5/2001 | Michelson | 606/96 |
| 6,228,900 B1 | 5/2001 | Shen | 522/153 |
| 6,234,705 B1 | 5/2001 | Troxell | 403/237 |
| 6,235,030 B1 | 5/2001 | Zucherman | 606/61 |
| 6,238,397 B1 | 5/2001 | Zucherman | 606/61 |
| 6,261,296 B1 | 7/2001 | Aebi | 606/90 |
| 6,280,444 B1 | 8/2001 | Zucherman | 606/61 |
| 6,293,949 B1 | 9/2001 | Justis | 606/61 |
| 6,299,642 B1 * | 10/2001 | Chan | 623/16.11 |
| 6,306,136 B1 | 10/2001 | Baccelli | 606/61 |
| 6,332,882 B1 | 12/2001 | Zucherman | 606/61 |
| 6,332,883 B1 | 12/2001 | Zucherman | 606/61 |
| 6,352,537 B1 | 3/2002 | Strnad | 606/61 |
| 6,368,351 B1 * | 4/2002 | Glenn et al. | 623/17.15 |
| 6,371,984 B1 | 4/2002 | Van Dyke | 623/11.11 |
| 6,379,355 B1 | 4/2002 | Zucherman | 606/61 |
| 6,383,186 B1 | 5/2002 | Michelson | 606/69 |
| 6,395,030 B1 | 5/2002 | Songer | 623/17.11 |
| 6,398,783 B1 | 6/2002 | Michelson | 606/70 |
| 6,402,756 B1 | 6/2002 | Ralph | 606/71 |
| 6,416,776 B1 | 7/2002 | Shamie | 424/423 |
| 6,419,676 B1 | 7/2002 | Zucherman | 606/61 |
| 6,419,677 B2 | 7/2002 | Zucherman | 606/61 |
| 6,419,703 B1 | 7/2002 | Fallin | 623/17.11 |
| 6,428,542 B1 | 8/2002 | Michelson | 606/70 |
| 6,436,145 B1 | 8/2002 | Miller | 623/20.34 |
| 6,440,169 B1 | 8/2002 | Elberg et al. | 623/17.16 |
| 6,451,019 B1 | 9/2002 | Zucherman | 606/61 |
| 6,451,020 B1 | 9/2002 | Zucherman | 606/61 |
| 6,454,771 B1 | 9/2002 | Michelson | 606/70 |
| 6,454,807 B1 * | 9/2002 | Jackson | 623/17.15 |
| 6,458,131 B1 | 10/2002 | Ray | 606/61 |
| 6,478,796 B2 | 11/2002 | Zucherman | 606/61 |
| 6,500,178 B2 | 12/2002 | Zucherman | 606/61 |
| 6,514,256 B2 | 2/2003 | Zucherman | 606/61 |
| 6,527,776 B1 | 3/2003 | Michelson | 606/70 |
| 6,558,423 B1 | 5/2003 | Michelson | 623/17.11 |
| 6,558,686 B1 | 5/2003 | Darouiche | 424/423 |
| 6,565,570 B2 | 5/2003 | Sterett | 606/69 |
| 6,565,605 B2 | 5/2003 | Goble | 623/17.11 |
| 6,579,318 B2 | 6/2003 | Varga | 623/17.11 |
| 6,579,319 B2 | 6/2003 | Goble | 623/17.11 |
| 6,582,433 B2 | 6/2003 | Yun | 606/61 |
| 6,592,586 B1 | 7/2003 | Michelson | 606/71 |
| 6,610,091 B1 | 8/2003 | Reiley | 623/17.11 |
| 6,620,163 B1 | 9/2003 | Michelson | 606/61 |
| 6,626,944 B1 | 9/2003 | Taylor | 623/17.16 |
| 6,641,585 B2 | 11/2003 | Sato et al. | 606/61 |
| 6,652,527 B2 | 11/2003 | Zucherman | 606/61 |
| 6,652,534 B2 | 11/2003 | Zucherman | 606/102 |
| 6,669,729 B2 | 12/2003 | Chin | 623/17.11 |
| 6,695,842 B2 | 2/2004 | Zucherman | 606/61 |
| 6,699,246 B2 | 3/2004 | Zucherman | 606/61 |
| 6,699,247 B2 | 3/2004 | Zucherman | 606/61 |
| 6,712,819 B2 | 3/2004 | Zucherman | 606/61 |
| 6,712,852 B1 | 3/2004 | Chung | 623/17.11 |
| 6,730,127 B2 | 5/2004 | Michelson | 623/17.16 |
| 6,746,485 B1 | 6/2004 | Zucherman | 623/17.16 |
| 6,752,831 B2 | 6/2004 | Sybert | 623/13.17 |
| 6,761,720 B1 | 7/2004 | Senegas | 606/61 |
| 6,764,491 B2 | 7/2004 | Frey et al. | 606/85 |
| 6,773,460 B2 * | 8/2004 | Jackson | 623/17.15 |
| 6,783,527 B2 | 8/2004 | Drewry | 606/61 |
| 6,796,983 B1 | 9/2004 | Zucherman | 606/61 |
| 6,800,670 B2 | 10/2004 | Shen | 522/153 |
| 6,811,567 B2 | 11/2004 | Reiley | 623/17.11 |
| 6,902,566 B2 | 6/2005 | Zucherman | 606/61 |
| 6,926,728 B2 | 8/2005 | Zucherman et al. | 606/190 |
| 6,936,050 B2 | 8/2005 | Michelson | 606/61 |
| 6,936,051 B2 | 8/2005 | Michelson | 606/61 |
| 6,949,123 B2 | 9/2005 | Reiley | 623/17.11 |
| 6,969,390 B2 | 11/2005 | Michelson | 606/61 |
| 6,972,019 B2 | 12/2005 | Michelson | 606/61 |
| 6,974,478 B2 | 12/2005 | Reiley et al. | 623/17.11 |
| 7,025,789 B2 | 4/2006 | Chow et al. | 623/21.11 |
| 7,041,105 B2 | 5/2006 | Michelson | 606/71 |
| 7,041,135 B2 | 5/2006 | Michelson | 623/17.11 |
| 7,041,136 B2 | 5/2006 | Goble et al. | 623/17.11 |
| 7,044,952 B2 | 5/2006 | Michelson | 606/71 |
| 7,048,736 B2 | 5/2006 | Robinson et al. | 606/61 |
| 7,063,701 B2 | 6/2006 | Michelson | 606/73 |
| 7,063,702 B2 | 6/2006 | Michelson | 606/73 |
| 7,074,237 B2 | 7/2006 | Goble et al. | 623/17.11 |
| 7,077,844 B2 | 7/2006 | Michelson | 606/71 |
| 7,087,084 B2 | 8/2006 | Reiley | 623/17.11 |
| 7,090,698 B2 | 8/2006 | Goble et al. | 623/17.11 |
| 7,097,645 B2 | 8/2006 | Michelson | 606/71 |
| 7,101,375 B2 | 9/2006 | Zucherman et al. | 606/61 |
| 7,101,398 B2 | 9/2006 | Dooris et al. | 623/13.11 |
| 7,112,202 B2 | 9/2006 | Michelson | 606/71 |
| 7,115,130 B2 | 10/2006 | Michelson | 606/71 |
| 7,163,561 B2 | 1/2007 | Michelson | 623/17.16 |
| 7,306,628 B2 * | 12/2007 | Zucherman et al. | 623/17.11 |
| 2001/0018614 A1 | 8/2001 | Bianchi | |
| 2002/0133155 A1 | 9/2002 | Ferree | |
| 2002/0151895 A1 | 10/2002 | Soboleski | |
| 2002/0183756 A1 | 12/2002 | Michelson | |
| 2003/0040746 A1 | 2/2003 | Mitchell | |
| 2004/0006391 A1 | 1/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0087948 A1 | 5/2004 | Suddaby | |
| 2004/0116927 A1 | 6/2004 | Graf | |
| 2004/0122427 A1 | 6/2004 | Holmes | |
| 2004/0143268 A1 | 7/2004 | Falahee | |
| 2004/0181229 A1 | 9/2004 | Michelson | |
| 2004/0186475 A1 | 9/2004 | Falahee | |
| 2004/0210313 A1 | 10/2004 | Michelson | |
| 2004/0230201 A1 | 11/2004 | Yuan | |
| 2004/0230304 A1 | 11/2004 | Yuan | |
| 2004/0236334 A1 | 11/2004 | Michelson | |
| 2004/0236335 A1 | 11/2004 | Michelson | |
| 2005/0027297 A1 | 2/2005 | Michelson | |
| 2005/0027298 A1 | 2/2005 | Michelson | |

FOREIGN PATENT DOCUMENTS

| | | |
|---|---|---|
| DE | 2821678 A1 | 4/1980 |
| DE | 3113142 A1 | 1/1982 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |

| | | |
|---|---|---|
| EP | 0307241 B1 | 12/1992 |
| EP | 0677277 A2 | 10/1995 |
| EP | 0767636 B1 | 4/1997 |
| EP | 1138268 A1 | 10/2001 |
| FR | 2623085 | 5/1989 |
| FR | 2681525 A1 | 3/1993 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| GB | 780652 | 8/1957 |
| JP | 10-179622 | 7/1998 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 95/35067 | 12/1995 |
| WO | WO 96/08206 A1 | 3/1996 |
| WO | WO 96/39975 | 12/1996 |
| WO | WO 98/48717 | 11/1998 |
| WO | WO 98/55038 | 12/1998 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/53126 | 9/2000 |
| WO | WO 01/26566 A1 | 4/2001 |
| WO | WO 01/28442 A1 | 4/2001 |
| WO | WO 02/34120 A2 | 5/2002 |
| WO | WO 02/051326 | 7/2002 |
| WO | WO 02/085226 A1 | 10/2002 |
| WO | WO 03/057055 A1 | 7/2003 |
| WO | WO 03/101350 A1 | 12/2003 |
| WO | WO 2004/071358 A1 | 8/2004 |
| WO | WO 2004/098465 A1 | 11/2004 |

OTHER PUBLICATIONS

Waldemar Link brochure entitled "Wirbelsäulen-Chirurgie: Instrumentarium Und Implantate Zur Wirbelsäulen-Chirurgie (Spinal Surgery: Instrumentation and Implants for Spinal Surgery)," Waldemar Link, Hamburg, Germany, 4 pages.

Tsuji, Haruo, et al., "Ceramic Interspinous Block (CISB) Assisted Anterior Interbody Fusion," Journal of Spinal Disorders, vol. 3, No. 1, pp. 77-86, Raven Press, Ltd., New York (1990).

Porter, Richard W., "Spinal Stenosis and Neurogenic Claudication," Spine, vol. 21, No. 17, pp. 2046-2052, Lippincott-Raven Publishers (1996).

* cited by examiner

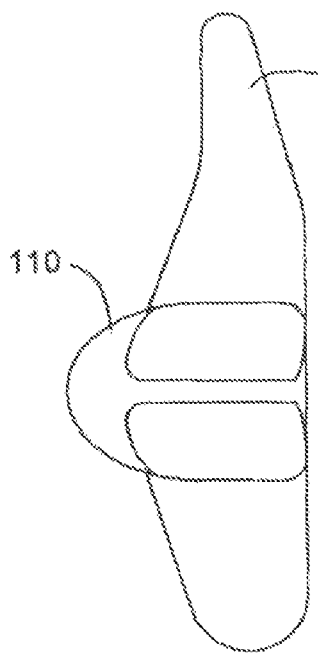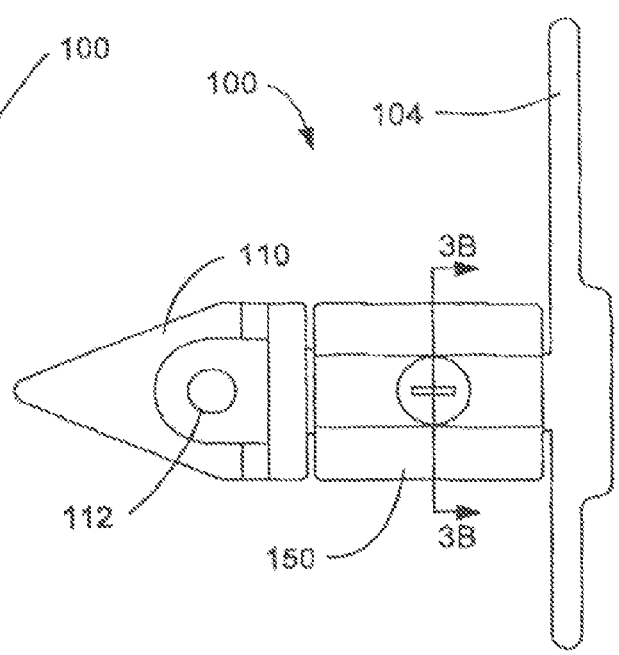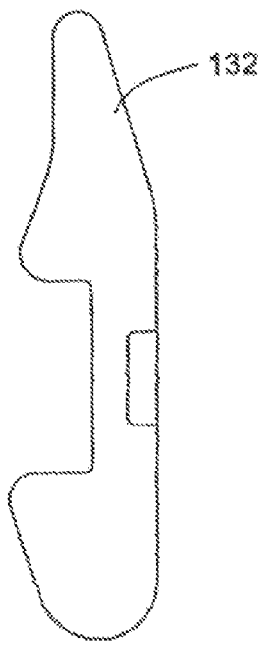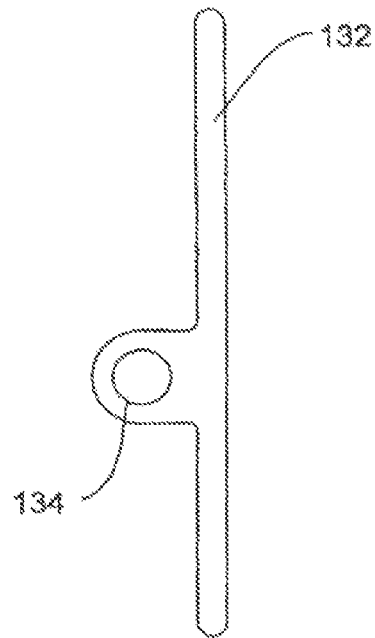
FIG. - 1B    FIG. - 1C
FIG. - 1D    FIG. - 1E

INTERSPINOUS PROCESS APPARATUS AND METHOD WITH A SELECTABLY EXPANDABLE SPACER

CLAIM OF PRIORITY

This application is a continuation of Ser. No. 10/684,847, filed Oct. 14, 2003, which claims benefit to U.S. Provisional Application No. 60/421,921, filed Oct. 29, 2002, which are incorporated herein by reference in their entireties.

CROSS REFERENCES TO RELATED APPLICATION

This application is related to U.S. patent application Ser. No. 10/037,236, filed Nov. 9, 2001, which is related to U.S. patent application Ser. No. 09/799,215, filed Mar. 5, 2001, now U.S. Pat. No. 7,101,375, issued Sep. 5, 2006, which is a related to U.S. patent application Ser. No. 09/179,570, filed Oct. 27, 1998, now U.S. Pat. No. 6,048,342, issued Apr. 11, 2000, which is related to U.S. patent application Ser. No. 09/175,645, filed Oct. 20, 1998, now U.S. Pat. No. 6,068,630, issued May 30, 2000. This application is also related to U.S. Pat. No. 5,836,948, issued Nov. 17, 1998 and U.S. Pat. No. 5,860,977, issued Jan. 19, 1999. All of the above are incorporated herein by reference.

FIELD OF THE INVENTION

This invention relates to an apparatus and method for adjustably distracting the spinous process of adjacent vertebrae.

BACKGROUND OF INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk, and arms to the pelvis and legs, (2) complex physiological motion between these parts, and (3) protection of the spinal cord and the nerve roots.

As the population ages, it is anticipated that there will be an increase in adverse spinal conditions characteristic in older persons. For example, with aging comes an increase in spinal stenosis (including, but not limited to, central canal and lateral stenosis), the thickening of the bones that make up the spinal column, and facet antropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals, and, in particular, for the elderly.

In addition, there are a variety of other ailments that can cause back pain in patients of all ages. For these ailments it is also desirable to eliminate such pain without major surgery.

Accordingly, there is a need for a method for alleviating such conditions that is minimally invasive, can be tolerated by patients of all ages (in particular, the elderly), can be performed on an out-patient basis, and allows adjustments both during and after surgery to minimize patient discomfort. There is a further need for an apparatus with which to apply the method.

BRIEF DESCRIPTION OF THE DRAWINGS

FIGS. 1A-1F. FIG. 1A is a front plan view of one embodiment of an apparatus with a selectably expandable spacer; FIG. 1B is a left side view of the apparatus of FIG. 1A; FIG. 1C is a front plan view of the apparatus of FIG. 1A including a selectably expandable spacer, a main body and a first wing; FIG. 1D is a left side view of the second wing of the apparatus of FIG. 1A; FIG. 1E is a front plan view of the second wing of the apparatus of FIG. 1A; FIG. 1F is an end view of the selectably expandable spacer of the apparatus of FIG. 1A.

FIG. 2A is a right side view of an embodiment of the selectably adjustable spacer in an unexpanded position. FIG. 2B is a right side view of an embodiment of the selectably adjustable spacer in a fully expanded position.

FIG. 3A is a right side cross-sectional view of an embodiment of the selectably adjustable spacer in an unexpanded position. FIG. 3B is a left side cross-sectional view of an embodiment of the selectably adjustable spacer in a fully expanded position.

FIG. 6A is a right side view of an alternative embodiment of the selectably expandable spacer with a jack expansion mechanism in an unexpanded position. FIG. 6B is a right side view of an alternative embodiment of the selectably expandable spacer with a jack expansion mechanism in a fully expanded position.

DETAILED DESCRIPTION OF THE PREFERRED EMBODIMENT

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 1A:
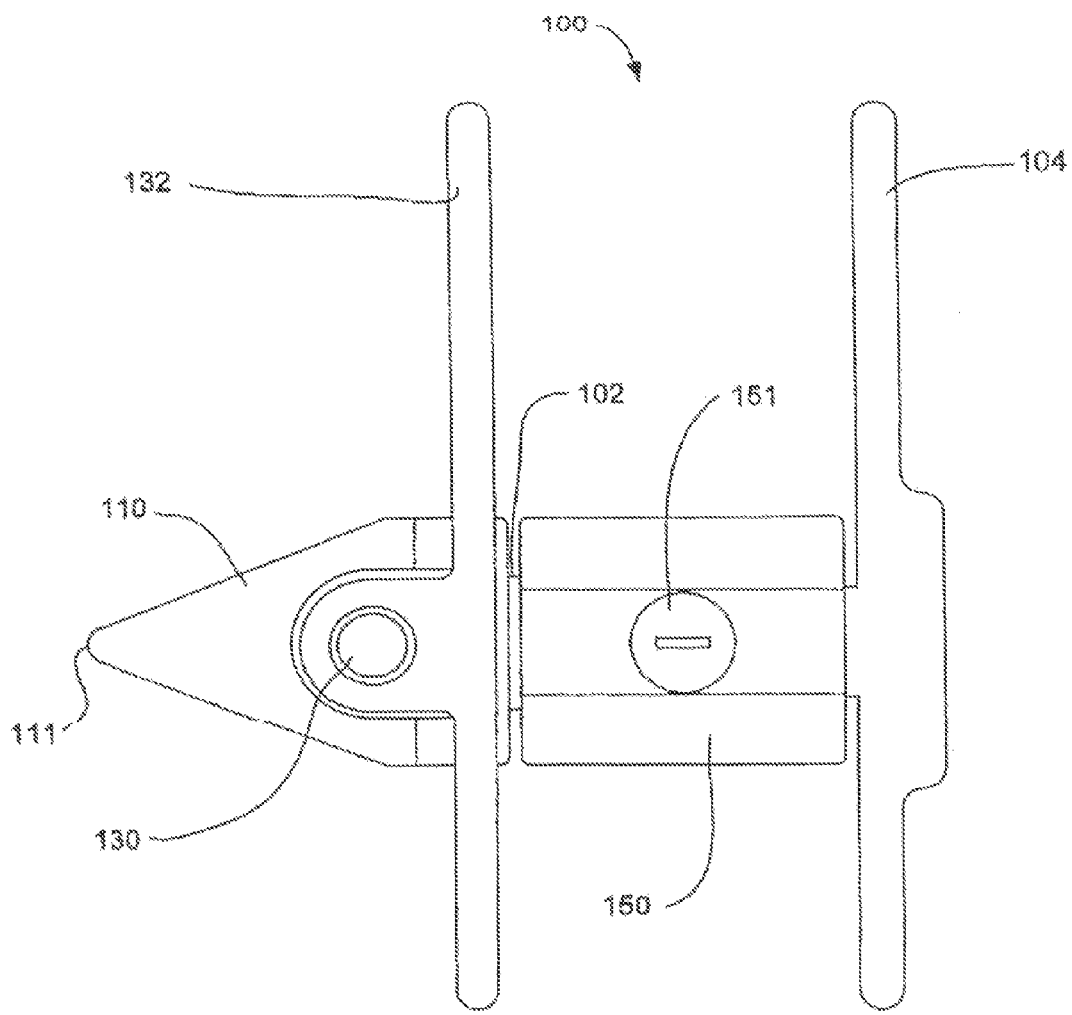
Figure 1F:
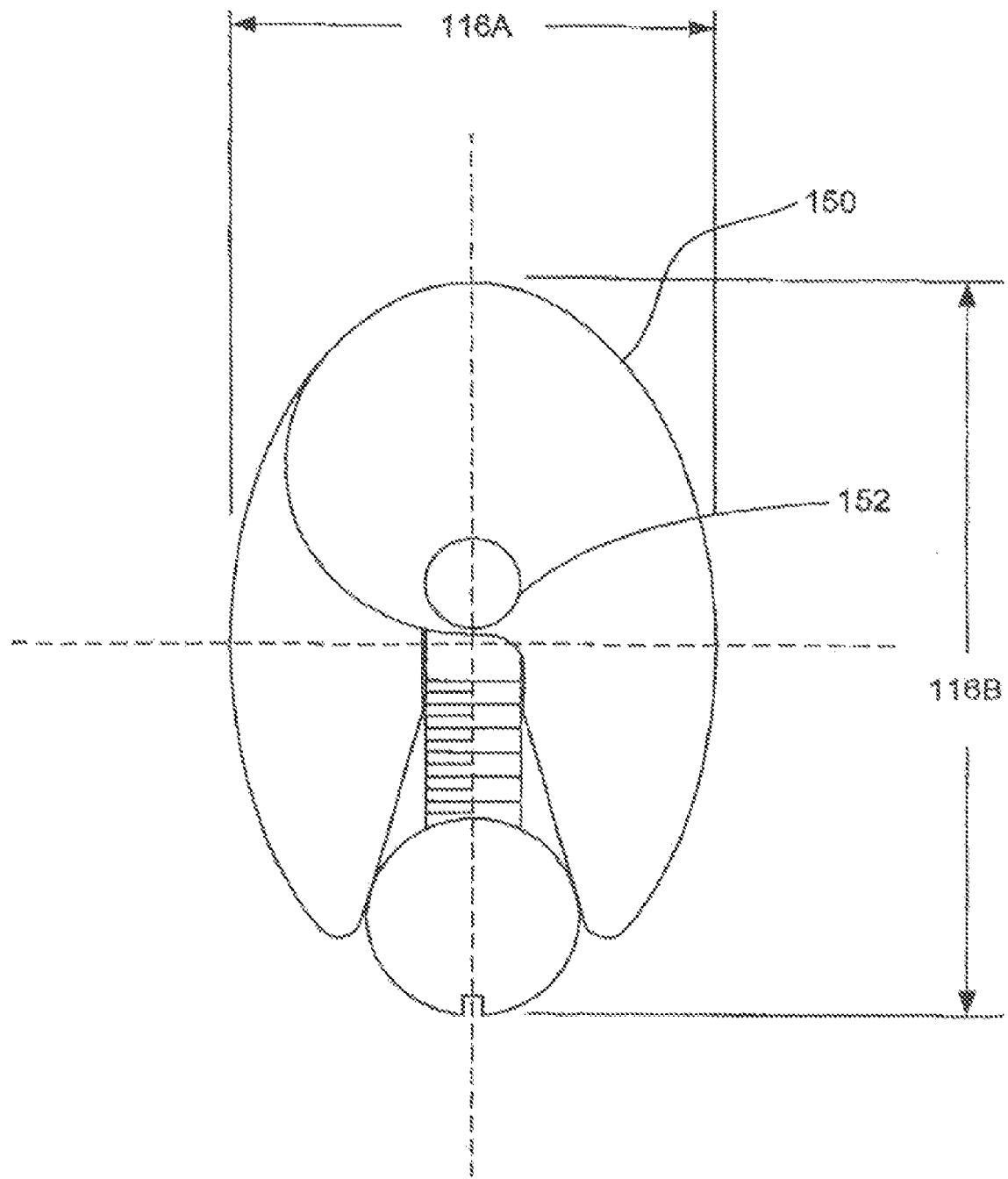

FIGS. 1A-1F illustrate an embodiment of an apparatus, or implant 100, suitable for use with the method of this invention. The implant 100 includes a first wing 104, a selectably expandable spacer 150 and a lead-in tissue expander or distraction guide 110. The implant further includes, as required, a second wing 132. As can be seen in FIG. 1A, a shaft 102 extends from the first wing 104 and is the body that connects the first wing to the distraction guide 110. Also, as can be seen in FIGS. 1A and 1B, the guide 110 in this particular embodiment is pointed in order to allow the implant to be inserted between, and, if necessary, to distract adjacent spinous processes. In this particular embodiment, the guide 110 has a wedge-shaped cross-section, expanding from the distal end 111 to the area where the second wing 132 can be optionally secured to the guide. FIGS. 1B and 1C illustrate an embodiment of the implant 100 with only a first wing 104.

As required, implant 100 can include a second wing 132 which fits over the guide 110 and is secured by a bolt 130 placed through aperture 134 of the second wing 132 to the threaded bore 112 located in the guide 110. As implanted, the first wing 104 is located adjacent to first sides of the spinous processes and the second wing 132 is located adjacent to second sides of the same spinous processes.

The spacer 150 is rotatably mounted about a shaft 102. The spacer 150 is positioned between the first wing 104 and the guide 110. The tissue expander 110 guides the spacer 150 into position between the spinous process of adjacent vertebrae. The spacer 150 includes a slotted sphere 151 that when rotated is positioned along a lead-screw, expanding or collapsing the spacer.

FIGS. 1F, 2A-B, 3A-B, and 5 illustrate a preferred embodiment of the spacer 150 wherein the shape of the spacer 150 is oval or elliptical in cross-section, although it can alternatively be circular or ovoid or race-track shaped in cross-section. It is to be understood that the spacer 150 can have other shapes as described throughout the specification and be within the spirit and scope of the invention. In a preferred embodiment, the spacer 150 includes a bore 152 extending the length of the spacer 150. The bore 152 of the spacer 150 is received over the shaft 102 of the implant 100 so that, as described above, the spacer can be rotated about the shaft 102. In these embodiments, the spacer 150 can have minor and major dimensions as follows:

| Minor Dimension (116a) | Major Dimension (116b) |
|---|---|
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

One advantage of the use of the spacer 150, as depicted in the embodiment of FIG. 1A, is that the spacer 150 can be partially rotated and repositioned with respect to the first wing 104 in order to optimize positioning of the implant 100 between spinous processes. It is to be understood that the cortical bone or the outer bone of the spinous processes is stronger at an anterior position adjacent to the vertebral bodies of the vertebra than at a position distally located from the vertebral bodies. Also, biomechanically for load bearing, it is advantageous for the spacer 150 to be close to the vertebral bodies. In order to facilitate this and to accommodate the anatomical form of the bone structures, as the implant is inserted between the spinous processes and/or urged toward the vertebral bodies, the spacer 150 rotates relative to the wings, such as wing 104, so that the spacer 150 is optimally positioned between the spinous processes, and the wing 104 is optimally positioned relative to the spinous processes.

In another embodiment, the spacer 150 has a cross-section with a major dimension and a minor dimension, wherein the major dimension is greater than the minor dimension, and, for example, less than about two times the minor dimension. It is to be understood that the spacer 150 can be fabricated from somewhat flexible and/or deflectable material.

In this embodiment the spacer is made out of a polymer, more specifically, the polymer is a thermoplastic. Still more specifically, the polymer is a polyketone known as polyetheretherketone (PEEK™). Still more specifically, the material is PEEK 450G, which is an unfilled PEEK approved for medical implantation available from Victrex of Lancashire, Great Britain. (Victrex is located at www.matweb.com or see Boedeker www.boedeker.com). other sources of this material include Gharda, located in Panoli, India (www.ghardapolymers.com).

The spacer 150 can be formed by extrusion, injection, compression molding and/or machining techniques. This material has appropriate physical and mechanical properties and is suitable for carrying and spreading the physical load between the spinous process. For example, in this embodiment, the PEEK has the following approximate properties:

| | |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the spacer 150 is manufactured from polyetheretherketon (PEEK™), available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics. The spacer can also be made of titanium.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials," PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

Other materials such as Bionate.R™, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 2A:
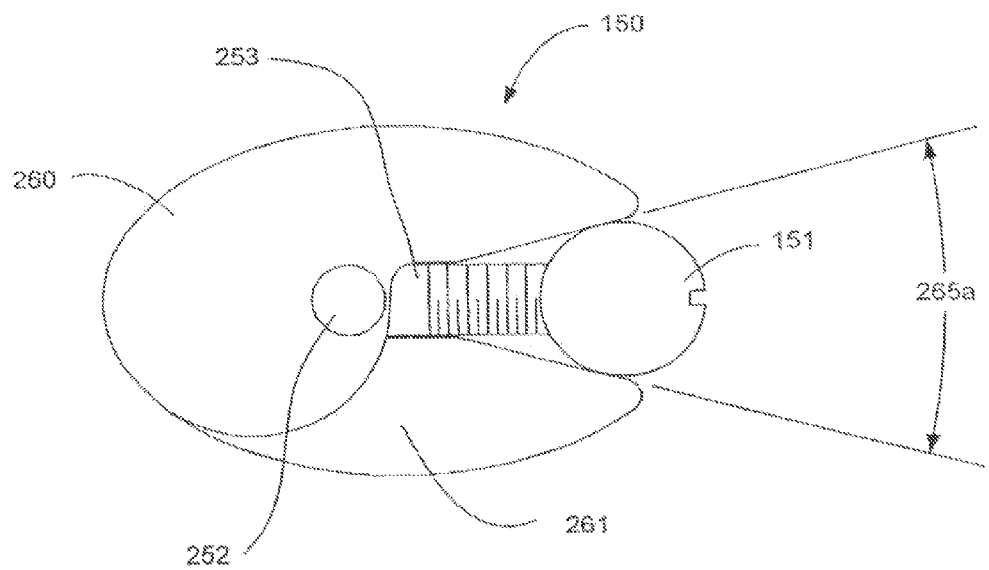
FIGS. 2A and 2B.

A preferred embodiment of the spacer is illustrated in FIGS. 2A-5. In FIGS. 2A and 2B the spacer 150 includes a first portion 260 pivotably or rotatably coupled with a second portion 261 by a hinge (shown in FIG. 4). Both the first portion 260 and the second portion 261 have tapered distal ends that form an acute angle between the two portions. FIG. 2A illustrates the acute angle 265a formed when the spacer 150 is in the unexpanded position. The first portion 260 has a bore 252 through which the shaft 102, shown in FIG. 1A, is received, connecting the first wing 104 with the guide 110 and connecting the spacer 150 with the implant 100. The bore 252 allows the spacer 150 to partially rotate about the shaft 102. The second portion 261 of the spacer 150 also has a bore that is located behind and aligned with the bore 252, shown in FIG. 2A. This bore is also received on the shaft 102 so that both the first and second portions of the spacer 150 can rotate about the shaft 102. A threaded screw 253 protrudes through the angle 265 a formed by the tapered distal ends of the portions. The end of the threaded screw 253 also has a bore that aligns with the bores of the first and second portions of the spacer 150 and is received on the shaft 102 and can rotate about the shaft 102. A slotted sphere 151 is connected with the distal end of screw 253. In the least expanded position, the slotted sphere 151 is at the farthest point of travel away from the proximal end of the screw 253 FIG. 2A.

Figure 2B:
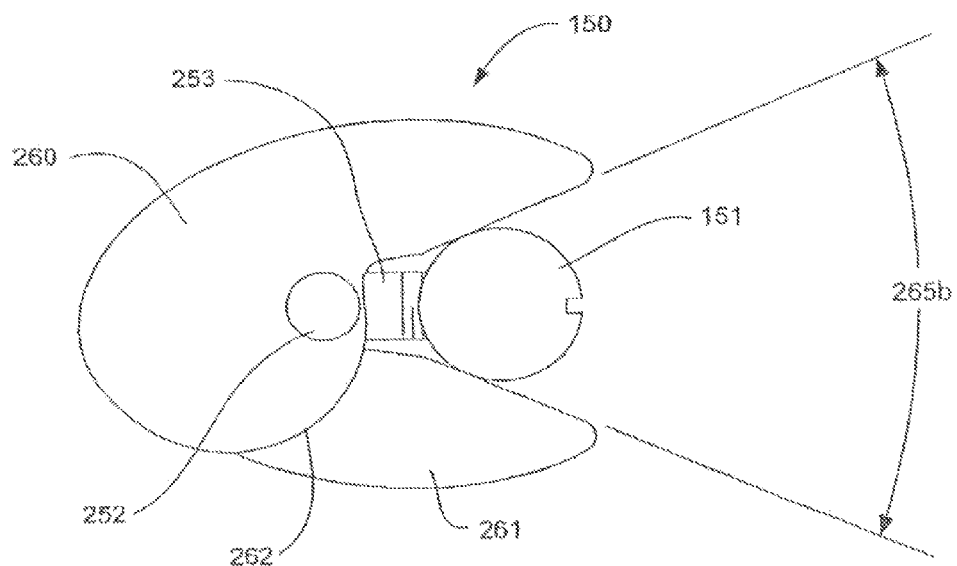

FIG. 2B illustrates the acute angle 265b formed when the spacer 150 is in the fully expanded position. The slotted sphere 151 is rotated such that the sphere travels toward the proximate end of the threaded screw 253. As the slotted sphere 151 travels toward the proximal end of the screw 253, the sphere 151 forces the tapered distal ends of the portions 260, 261 apart. As the distal ends of the portions are forced apart, the first portion 260 and the second portion 261 rotate in opposite directions about a common hinge 463 (shown in FIG. 4), sliding along the contact surface 262. As the acute angle formed by the distal ends of the portions increases, the height of the spacer 150 expands.

Figure 3A:
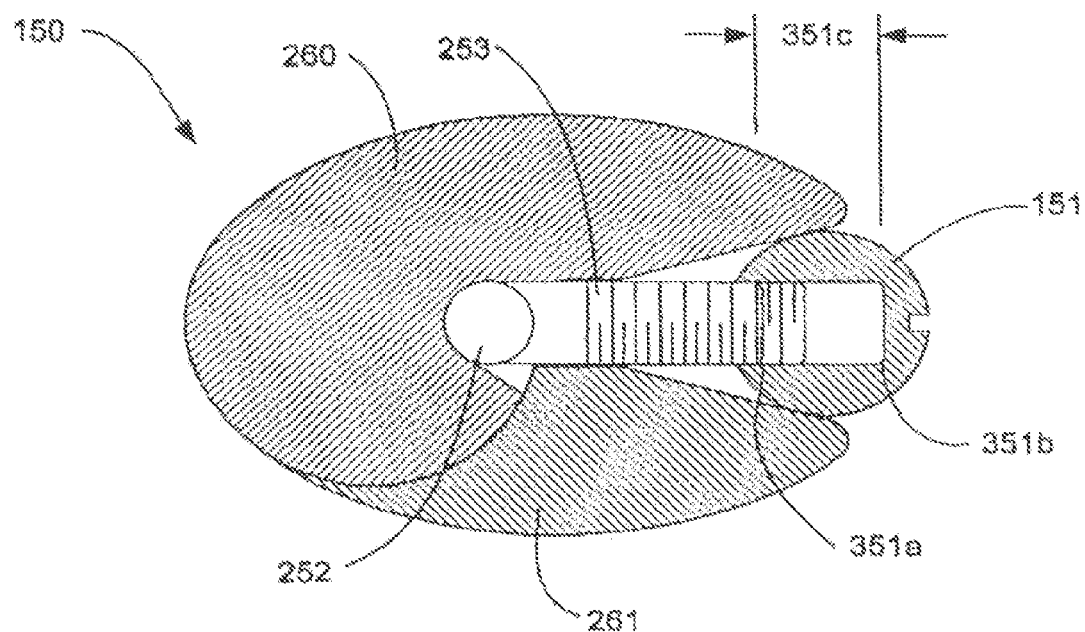
FIGS. 3A and 3B.
Figure 3B:
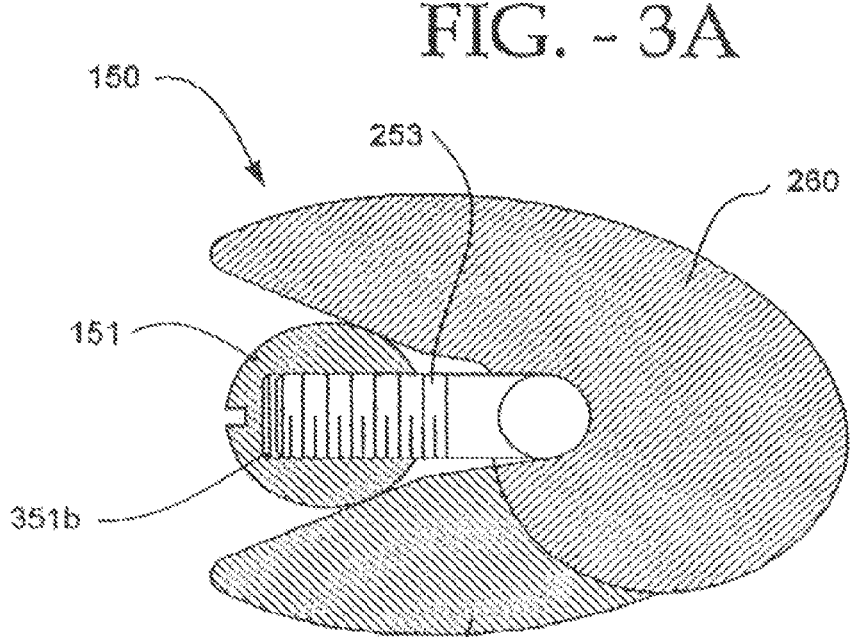

FIGS. 3A and 3B illustrate in cross-section the preferred embodiment of the selectably expandable spacer described in reference to FIGS. 2A and 2B. The slotted sphere 151 has a threaded cavity for receiving the threaded screw 253 when the sphere 151 is rotated. The slotted sphere 151 travels the distance 351c such that the distal end of the screw 253 moves from position 351a to position 351b along the threaded cavity of the sphere when adjusted from an unexpanded to a fully expanded position. When rotated in the opposite direction, the slotted sphere 151 moves away from the proximal end of the screw 253, collapsing the spacer 150. FIG. 3B illustrates the spacer 150 in a fully expanded position with the distal end of the screw 253 at the maximum position 351b in the threaded cavity of the slotted sphere 151. It is to be understood that portions the 260, 261 of the spacer 150 can be biased to the closed position shown in FIG. 3A. The biasing can be accomplished by a spring that is coiled in or about the bore of the spacer that receives the shaft 102. Such a spring would be connected to both of the portions 260, 261 of the spacer 150.

The first and second portions of the spacer 150 in combination, can have a cross-section that is elliptical, oval, ovoid, football-shaped, circular-shaped, rectangular with rounded ends (where the cross-section has two somewhat flattened surfaces and two rounded surfaces similar to the effect of a flattened ellipse) or race-track shaped. Further, the first and second portions can have different cross-sectional shapes relative to each other. At least the minor dimension (the height) of the spacer is between 6 mm and 14 mm. Typically, the minor outer dimension is one of 6 mm, 8 mm, 10 mm, 12 mm, and 14 mm. The different sizes and selectable expandability enable the spacer to accommodate different sized patients.

As discussed above, the spacer 150 and its components, including either the first or second portions, or both, can be made of a number of materials. Suitable materials can include polymers, such as, for example, polyetheretherketone (PEEK™), as well as other materials described above, including titanium. Such materials can be deflectable and flexible depending on the configuration of the spacer 150.

Further, the deflectable or flexible material can have a graduated stiffness to help gradually distribute the load when the spinous processes place a force upon the exterior surface of the spacer. This can be accomplished by forming multiple layers of the deflectable or flexible material with decreasing stiffness or hardness from the center of the spacer outwardly. Alternatively, the material can have a higher stiffness or hardness in the center of the inner spacer.

Figure 4:
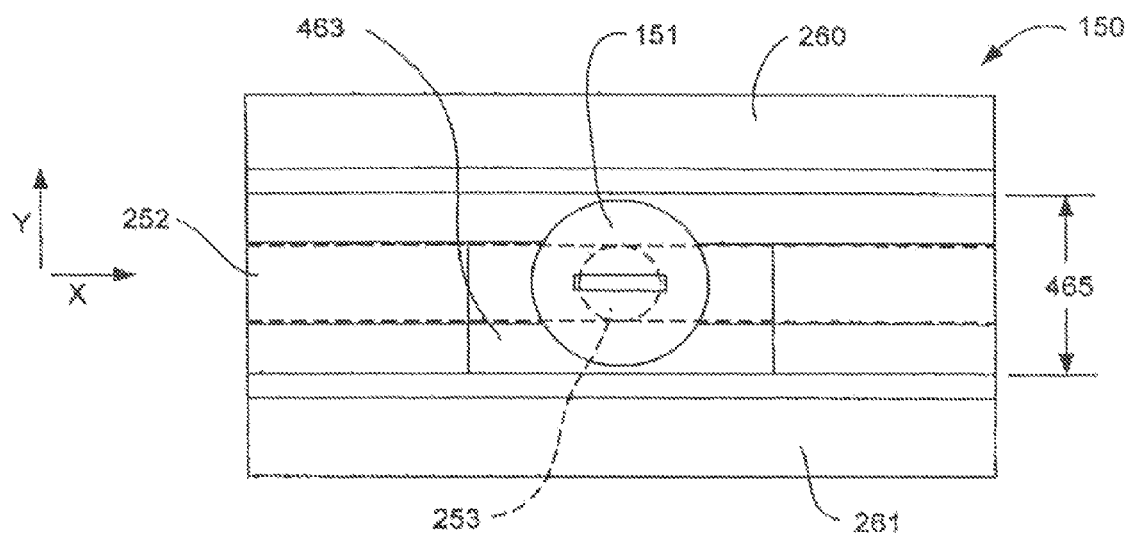
FIG. 4 is a front side view of an embodiment of the selectably adjustable spacer.

Referring to FIG. 4, the slotted sphere 151 is positioned approximately equidistant from a first and second ends of the spacer 150, distributing the parting force of the sphere 151 so as not to create disproportionate stress on either side of the spacer 150.

A hinge 463 couples a first portion 260 with a second portion 261, such that the two portions pivot about the hinge 463, expanding or collapsing the gap 465.

Figure 5A:
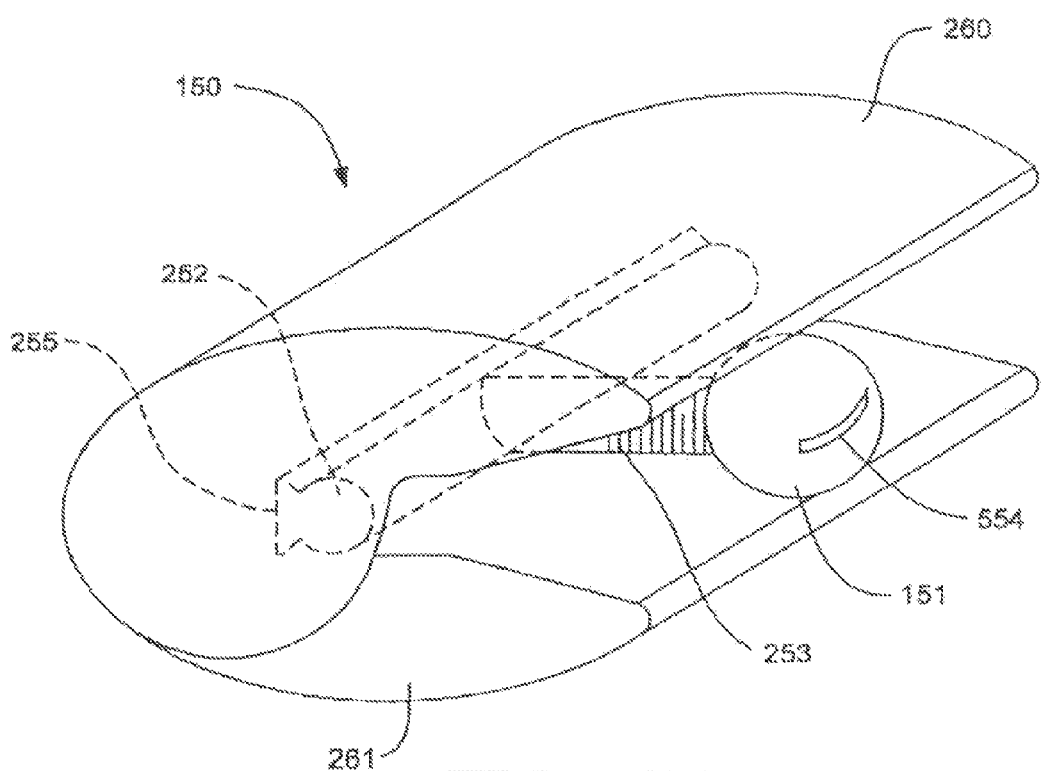
FIG. 5A is a perspective view of an embodiment of the selectably adjustable spacer.

A perspective view is provide in FIG. 5A, showing the clam-shape of the preferred embodiment of the spacer 150. The implant 100 is positioned between the adjacent vertebrae so as to permit access to the slot 554 from a posterior direction both during and after surgery. Post-surgery adjustment is made using a cannula inserted through the patient's back. Convenient access to the slot 554 is important for reducing patient discomfort and procedure complication.

The bore 252 provides a sleeve for the shaft 102, and also limits the rotation of the spacer 150 about the shaft 102. Limiting the rotation of the spacer 150 can be accomplished, for example, by providing a slot 255 in the bore 252 and a key on the shaft 102, or vice-versa. One of skill in the art can appreciate that different mechanisms and geometries can be used to limit spacer rotation. Reference is also made to a copending U.S. patent application entitled "Spinal Implants, Insertion Instruments, and Methods of Use," filed on Mar. 5, 2001, as U.S. patent application Ser. No. 09/799,470 (KLYC-1027 US1), which is incorporated herein by reference and which discloses an implant which has a spacer with a slot and an implantation tool that includes a probe that engages the slot in order to position the spacer relative to the implantation tool for desirable initial positioning of the space relative to the spinous processes. Such a mechanism can be used by itself or in addition to the above discussed keyway and key for purposes of positioning the sphere 151 so that the height of the spacer 150 can be selectively adjusted during the initial surgical procedure or thereafter, should such adjustment be desirable due, for example, to the need for more distraction between the spinous processes.

Figure 5B:
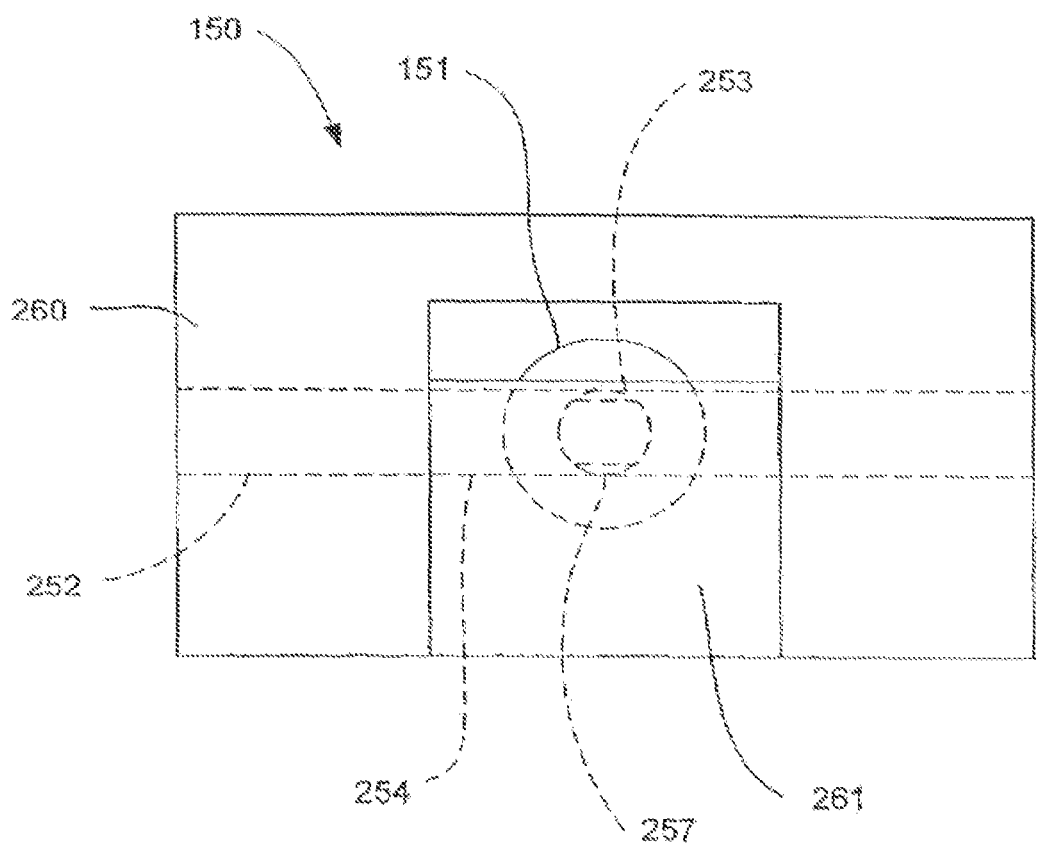
FIG. 5B is a back view of another embodiment of the spacer similar to that shown in FIG. 5A with a mechanism for allowing the spacer to expand.

FIG. 5B depicts the back of another embodiment of the spacer 150 of the implant 100 of the invention. FIG. 5B is similar to a back view of the embodiment depicted in FIG. 4. In FIG. 5B, the spacer 150 includes the first and second portions 260, 261, respectively. The first portion includes a bore 252 that receives the shaft 102 and the second portion includes bore 254 that also receives the shaft 102. In addition, the screw 253 is shown with a portion of the sphere 151 that is used to adjust the height of the spacer 150. The screw 253 includes a bore 257 that also receives the shaft 102. Thus, the first and second portions of the spacer and the screw are rotatable about the shaft.

Figure 6A:
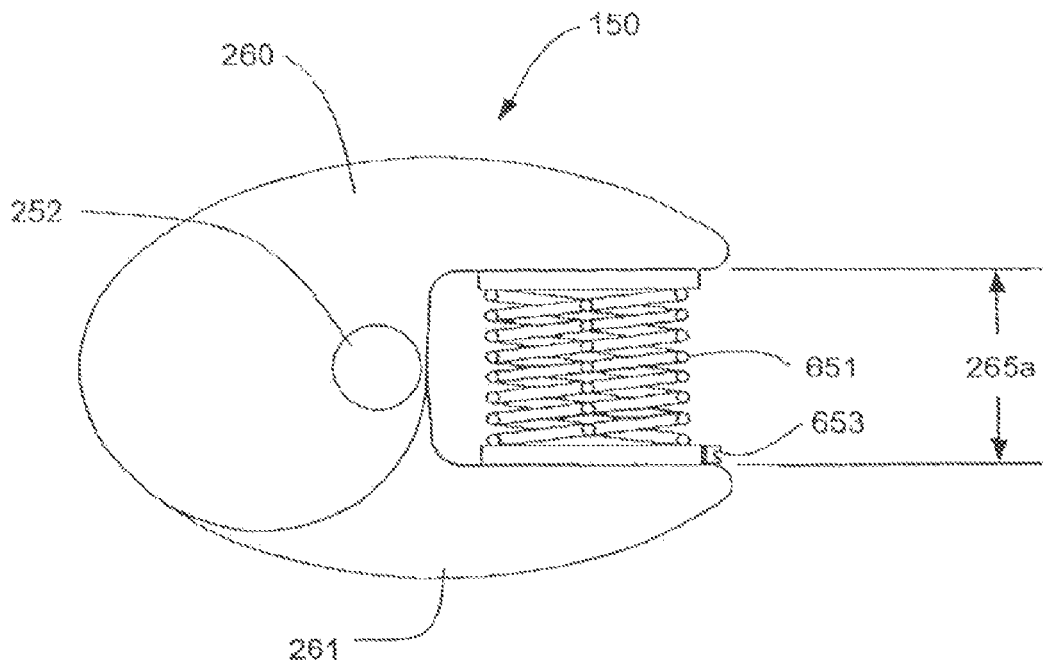
FIGS. 6A and 6B.
Figure 6B:
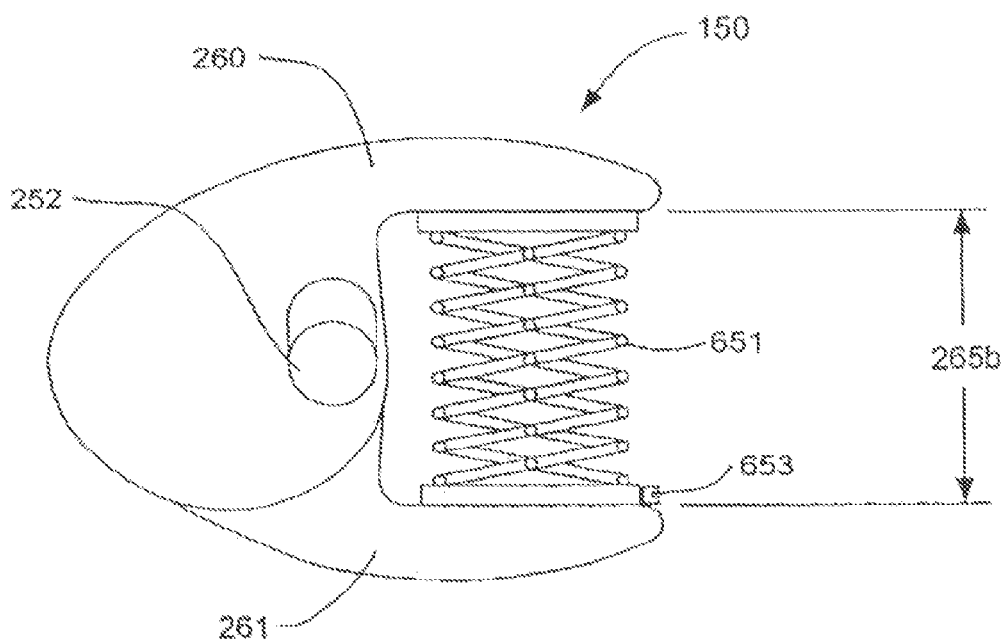

One of skill in the art can also appreciate the different expansion mechanisms that can be employed to expand the spacer 150. For example, an expansion mechanism could include: pistons, ratchets, cams, jacks, or other machines. FIGS. 6A and 6B illustrate one alternative embodiment in which a jack 651 is used to expand the spacer 150. The jack 651 is expanded or collapsed by rotating a slotted screw 653, thereby increasing or decreasing the gap 665. FIG. 6A shows the spacer 150 in an unexpanded position with a narrow gap 665a.

FIG. 6B illustrates another alternative embodiment utilizing a jack, whereby the hinge 462 can allow for translation of the first and second portions in the y-direction as well as for rotation about the hinge 462, thereby reducing the stresses on the side of the jack closest to the hinge caused by uneven compression when the gap 665b expands. For the embodiment in FIGS. 6A and 6B any of the above devices for allowing the first portion of the spacer to move relative to the second portion of the spacer can be employed, as well as other known methods, and be within the spirit and scope of the invention.

Figure 7:
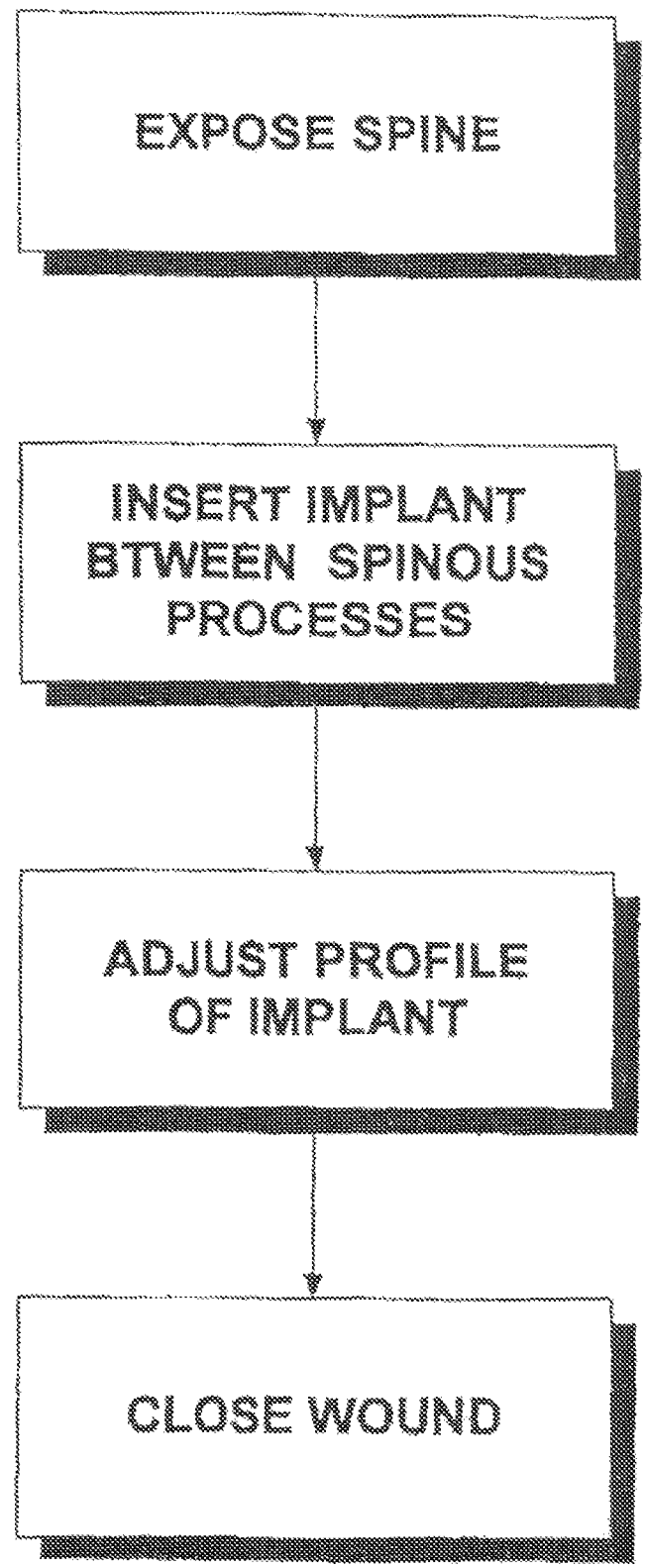
FIG. 7 is a block diagram demonstrating the steps for performing the method.

The preferred method for inserting the implant between adjacent vertebrae is block-diagramed in FIG. 7. The method requires that the spine by surgically exposed. The implant is then inserted between the spinous processes, with the wedge shape of the guide forcing tissue apart to create room for the implant. Once the implant is in place, with the spacer between adjacent vertebrae, the profile of the implant is adjusted by expanding or collapsing the spacer using a tool for operating the expansion mechanism. The wound is then closed.

The implant can subsequently be readjusted with the insertion of a cannula through which a tool is inserted for operating the expansion mechanism.

The embodiment of this apparatus as well as the several other apparatuses described herein, act to limit extension (backward bending) of the spine. These apparatuses, however, do not inhibit the flexion (forward bending) of the spinal column.

the foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

What is claimed is:

1. An implant adapted to be inserted between adjacent spinous processes, said implant including:
    a first member and a second member;
    said first member connected to said second member with a hinge;
    said first member adapted to be positioned adjacent to a first of the adjacent spinous processes, and the second member adapted to be positioned adjacent to a second of the adjacent spinous processes;
    a screw mechanism having a cam member rotatively engaged with a threaded shaft;
    said screw mechanism positioned between the first member and the second member; and
    wherein displacement of the cam member relative to the threaded shaft toward the hinge causes said cam member to urge the first member away from the second member in order to distract apart the first and second spinous processes.

2. The implant of claim 1 wherein the implant is V-shaped with the first member urged away from the second member.

3. The implant of claim 1 wherein said screw mechanism includes an inclined surface that when moved cause the first member to be urged away from the second member.

4. The implant of claim 1 wherein said screw mechanism includes a head with a slot that is adapted to receive a screwdriver.

5. The implant of claim 1 wherein at least one of said first members and said second members includes an inclined surface such that when the screw mechanism is operated the first member is urged away from the second member.

6. The implant of claim 1 wherein said first member and said second member have a first position wherein said first member and said second member are parallel to each other and a second position where said first member is disposed at an angle relative to said second member.

7. The implant of claim 1 wherein said cam member comprises a threaded cavity, constricted on one end, and wherein said threaded shaft extends into said threaded cavity.

8. The implant of claim 1 wherein the cam member comprises:
    a threaded cavity for receiving the threaded shaft, the cavity obstructed at one longitudinal end by a wall; and
    a tool-engaging feature configured to engagingly receive a driving tool, the tool-receiving feature disposed opposite said cavity relative to said wall.

9. A method for implanting an implant between adjacent spinous processes, the method including the steps of:
    laterally inserting the implant between adjacent spinous processes;
    wherein the implant includes:
        a first member and a second member;
        said first member connected to said second member with a hinge;
        said first member adapted to be positioned adjacent to a first of the adjacent spinous processes, and the second member adapted to be positioned adjacent to a second of the adjacent spinous processes;
        a screw mechanism;
        said screw mechanism positioned between the first member and the second member;
    operating the screw mechanism so that the first member is urged away from the second member in order to distract apart the first and second spinous processes.

10. The method of claim 9 wherein said operating step occurs after the inserting step and while the implant is located between the spinous processes.

11. The method of claim 9 wherein said operating step causes an inclined surface to be urged between the first member and the second member in order to urge apart the first member from the second member.

12. The method of claim 9 wherein said operating step includes engaging a screw driver with the screw mechanism to operate the screw mechanism.

13. The method of claim 10 wherein said operating step includes positioning a screw driver head adjacent to the spinous processes and engaging the screw mechanism in order to urge apart the first member from the second member.

14. The method of claim 9 wherein the step of operating said screw mechanism causes said first member and said second member to form a V-shape.

15. The method of claim 9 wherein said operating step includes re-operating the screw mechanism after initially operating the screw mechanism in order to reposition the first member relative to the second member.

16. The method of claim 15 wherein said re-operating step can occur after the implant is initially implanted between spinous processes and wherein with said re-operating step the distraction between spinous processes is changed.

17. The method of claim 9 wherein one of said first members and second members include an inclined surface such that as the screw mechanism is operated the inclined surface causes the first member to be urged away from the second member.

18. The method of claim 9 wherein said operating step causes the first member and said second member to be urged from a first configuration wherein said first member and said second member are parallel to each other, to a second configuration wherein said first member is provided at an angle relative to said second member.

19. The method of claim 9 wherein said operating the screw mechanism comprises applying a distraction force at the first and second adjacent spinous processes.

20. The method of claim 9 wherein said operating the screw mechanism comprises engaging the first and second spinous processes respectively, to distract apart the first and second spinous processes.

21. The method of claim 9 wherein the implant further comprises a wing coupled to the first and second members, and wherein said laterally inserting the implant comprises disposing the wing alongside the first spinous process.

22. An implant adapted to be inserted between adjacent spinous processes, said implant including:
   a first member and a second member;
      said first member connected to said second member with a hinge;
      said first member adapted to be positioned adjacent to a first of the adjacent spinous processes, and the second member adapted to be positioned adjacent to a second of the adjacent spinous processes;
      a screw mechanism having a tool-receiving cap rotatively engaged on a threaded shaft and moveable therealong; said tool receiving cap adapted to engage a driver tool;
      said screw mechanism positioned between the first member and the second member; and
      wherein when the screw mechanism is operated, the first member is urged away from the second member in order to distract apart the first and second spinous processes.

23. An implant adapted to be inserted between adjacent spinous processes, comprising:
   a shaft extending along a longitudinal axis from a proximal end portion to a distal end portion;
   a wing disposed proximate said proximal end portion and generally transverse to said axis;
   a distraction guide disposed proximate said distal end portion and tapering away from said proximal end portion in a direction generally parallel to said axis;
   a spacer disposed between said wing and said distraction guide and comprising:
   a first member including a first longitudinal bore;
   a second member distinct from said first member and pivotally connected thereto by a hinge mechanism;
   said second member including a second longitudinal bore disposed in general alignment with said first longitudinal bore;
   a screw expansion mechanism positioned between the first and second members; said
      screw expansion mechanism operative to urge said first member to pivot away from said second member;
      wherein said shaft extends through said first and second longitudinal bores so as to couple said spacer to said shaft for rotation thereabout;
      wherein said first and second members are adapted to engage respective ones of the adjacent spinous processes, with said shaft extending through a sagittal plane defined by said adjacent spinous processes, so as to distract apart the adjacent spinous processes.

\* \* \* \* \*